(12) United States Patent
Kanniah et al.

(10) Patent No.: US 11,220,488 B2
(45) Date of Patent: Jan. 11, 2022

(54) CRYSTALLINE POLYMORPH OF PONESIMOD

(71) Applicant: TEVA PHARMACEUTICALS INTERNATIONAL GMBH, Jona (CH)

(72) Inventors: Sundara Lakshmi Kanniah, Vellore (IN); Kanhaiyalal, Greater Noida West (IN); Anantha Rajmohan Muthusamy, Sivakasi (IN)

(73) Assignee: TEVA PHARMACEUTICALS INTERNATIONAL GMBH, Jona (CH)

( * ) Notice: Subject to any disclaimer, the term of this patent is extended or adjusted under 35 U.S.C. 154(b) by 0 days.

(21) Appl. No.: 16/647,881

(22) PCT Filed: Sep. 7, 2018

(86) PCT No.: PCT/US2018/049907
§ 371 (c)(1),
(2) Date: Mar. 17, 2020

(87) PCT Pub. No.: WO2019/060147
PCT Pub. Date: Mar. 28, 2019

(65) Prior Publication Data
US 2020/0216405 A1   Jul. 9, 2020

(30) Foreign Application Priority Data

Sep. 19, 2017 (IN) .............................. 201711033131
Nov. 24, 2017 (IN) .............................. 201711042178
Jun. 15, 2018 (IN) .............................. 201811022445

(51) Int. Cl.
| A61K 31/426 | (2006.01) |
| A61P 17/06 | (2006.01) |
| A61P 37/06 | (2006.01) |
| C07D 277/54 | (2006.01) |
| A61P 37/00 | (2006.01) |

(52) U.S. Cl.
CPC .......... *C07D 277/54* (2013.01); *A61K 31/426* (2013.01); *A61P 17/06* (2018.01); *A61P 37/06* (2018.01); *A61P 37/00* (2018.01); *C07B 2200/13* (2013.01)

(58) Field of Classification Search
CPC .............. C07D 277/54; C07B 2200/13; C07B 2300/13; A61K 31/426; A61P 17/06; A61P 37/06
See application file for complete search history.

(56) References Cited

U.S. PATENT DOCUMENTS

| 9,062,014 B2 | 6/2015 | Bonham et al. |
| 9,340,518 B2 | 5/2016 | Herse |

FOREIGN PATENT DOCUMENTS

| WO | 2005054215 A1 | 6/2005 |
| WO | 2008062376 A2 | 5/2008 |
| WO | 2017107972 A1 | 6/2017 |

OTHER PUBLICATIONS

Olsson et al. Oral ponesimod in relapsing-remitting multiple sclerosis: a randomised phase II trial. J. Neurol. Neurosurg. Psychiatry, 2014; 85: 1198-1208.*
Extended European Search Report issued in corresponding Appl. No. EP 18857988.2 dated Dec. 10, 2020 (6 pages).
International Search Report and Written Opinion of the International Searching Authority issued in corresponding Appl. No. PCT/US18/49907 dated Nov. 19, 2018 (9 pages).

* cited by examiner

*Primary Examiner* — Theodore R. Howell
(74) *Attorney, Agent, or Firm* — Carter, DeLuca & Farrell LLP (57) ABSTRACT

The present disclosure encompasses crystalline polymorphs of Ponesimod, processes for preparation thereof, and pharmaceutical compositions thereof.

9 Claims, 7 Drawing Sheets

Fig. 1. X-Ray Powder Diffraction Pattern of Ponesimod Form T1

*Fig. 2.* X-Ray Powder Diffraction Pattern of Ponesimod Form T2

Fig. 3. X-Ray Powder Diffraction Pattern of Ponesimod Amorphous Form

Fig. 4. Solid State $^{13}$C NMR spectrum of Ponesimod Form T1 at the range of 200-0 ppm Fig. 5. Solid State $^{13}$C NMR spectrum of Ponesimod Form T1 at the range of 200-100 ppm Fig. 6. Solid State $^{13}$C NMR spectrum of Ponesimod Form T1 at the range of 100-0 ppm

*Fig. 7.* X-Ray powder diffraction pattern (XRPD) of Ponesimod Form A, as disclosed in US patent No. 9,062,014 (figure 2)

CRYSTALLINE POLYMORPH OF PONESIMOD

CROSS REFERENCE TO RELATED APPLICATIONS

This application is a National Stage Application of, and claims priority to and the benefit of, International Patent Application No. PCT/US2018/049907 filed on Sep. 7, 2018, which, in turn, claims the benefit of, and priority to, Indian Application No. 201711033131 filed Sep. 19, 2017, Indian Application No. 201711042178 filed Nov. 24, 2017, and Indian Application No. 201811022445 filed Jun. 15, 2018, the entire disclosures of each of which are incorporated by reference herein.

FIELD OF THE INVENTION

The present disclosure encompasses crystalline polymorphs of Ponesimod, processes for preparation thereof, and pharmaceutical compositions thereof.

BACKGROUND OF THE INVENTION

Ponesimod chemical name is (R)-5-[3-chloro-4-(2,3-dihydroxy-propoxy)-benz[Z]ylidene]-2-([Z]-propylimino)-3-o-tolyl-thiazolidin-4-one), having the following chemical structure:

Ponesimod is a Sphingosine-1-phosphate receptor-1 ($S_1P_1$) agonist, under development for the treatment of certain pathologies, e.g.: autoimmune diseases.

The compound is described in PCT application WO 2005/054215. A process for its preparation is described in PCT application WO 2008/062376, as well as in WO 2014/027330. PCT applications WO 2010/046835 (U.S. Pat. No. 9,062,014) and WO 2017/107972 described crystalline forms of Ponesimod.

Polymorphism, the occurrence of different crystalline forms, is a property of some molecules and molecular complexes. A single molecule, like Ponesimod, may give rise to a variety of polymorphs having distinct crystal structures and physical properties like melting point, thermal behaviors (e.g., measured by thermogravimetric analysis—"TGA", or differential scanning calorimetry—"DSC"), X-ray diffraction (XRD) pattern, infrared absorption fingerprint, and solid state ($^{13}C$) NMR spectrum. One or more of these techniques may be used to distinguish different polymorphic forms of a compound.

Different salts and solid state forms (including solvated forms) of an active pharmaceutical ingredient may possess different properties. Such variations in the properties of different salts and solid state forms and solvates may provide a basis for improving formulation, for example, by facilitating better processing or handling characteristics, changing the dissolution profile in a favorable direction, or improving stability (polymorph as well as chemical stability) and shelf-life. These variations in the properties of different salts and solid state forms may also offer improvements to the final dosage form, for instance, if they serve to improve bioavailability. Different salts and solid state forms and solvates of an active pharmaceutical ingredient may also give rise to a variety of polymorphs or crystalline forms, which may in turn provide additional opportunities to assess variations in the properties and characteristics of a solid active pharmaceutical ingredient.

Discovering new solid state forms and solvates of a pharmaceutical product may yield materials having desirable processing properties, such as ease of handling, ease of processing, storage stability, and ease of purification or as desirable intermediate crystal forms that facilitate conversion to other polymorphic forms. New solid state forms of a pharmaceutically useful compound can also provide an opportunity to improve the performance characteristics of a pharmaceutical product. It enlarges the repertoire of materials that a formulation scientist has available for formulation optimization, for example by providing a product with different properties, e.g., a different crystal habit, higher crystallinity, or polymorphic stability, which may offer better processing or handling characteristics, improved dissolution profile, or improved shelf-life (chemical/physical stability). For at least these reasons, there is a need for additional solid state forms (including solvated forms) of Ponesimod.

SUMMARY OF THE DISCLOSURE

The present disclosure provides crystalline polymorphs of Ponesimod, processes for preparation thereof, and pharmaceutical compositions thereof. These crystalline polymorphs can be used to prepare other forms of Ponesimod.

In particular, the present disclosure relates to solid state forms of Ponesimod designated as Form T1 and Form T2 (defined herein). The present disclosure also provides the uses of any one or combination of the above described solid state forms of Ponesimod for preparing other solid state forms of Ponesimod.

The present disclosure further provides processes for preparing Ponesimod solid state forms thereof.

In another embodiment, the present disclosure provides any one of the above described crystalline polymorphs of Ponesimod for use in medicine, preferably for the treatment of autoimmune diseases.

The present disclosure also encompasses the uses of any one of the above described crystalline polymorphs of Ponesimod of the present disclosure for the preparation of pharmaceutical compositions and/or formulations.

In another aspect, the present disclosure provides pharmaceutical compositions comprising crystalline polymorphs of Ponesimod according to the present disclosure.

In yet another embodiment, the present disclosure encompasses pharmaceutical formulations comprising any one of the above described crystalline polymorphs of Ponesimod and/or combinations thereof, and at least one pharmaceutically acceptable excipient.

The present disclosure comprises processes for preparing the above mentioned pharmaceutical formulations of Ponesimod comprising any one of the above described crystalline polymorphs and at least one pharmaceutically acceptable excipient.

The crystalline polymorphs defined herein and/or combinations thereof as well as the pharmaceutical compositions or formulations of the crystalline polymorphs of Ponesimod may be used as medicaments, particularly for the treatment of autoimmune diseases.

The present disclosure also provides methods of treating autoimmune diseases, comprising administering a therapeutically effective amount of any one of the crystalline polymorphs of Ponesimod of the present disclosure, or at least one of the above pharmaceutical compositions or formulations, to a subject suffering from autoimmune diseases, or otherwise in need of the treatment.

The present disclosure also provides the uses of any one of the solid state forms of Ponesimod of the present disclosure, or at least one of the above pharmaceutical compositions or formulations, for the manufacture of medicaments for treating autoimmune diseases.

Autoimmune diseases preferably include those selected from the group consisting of: amyloidosis, ankylosing spondylitis, autoimmune hepatitis, autoimmune retinopathy, autoimmune utricaria, celiac disease, chronic inflammatory demyelinating polyneuropathy, Crohn's disease, endometriosis, fibromyalgia, Graves' disease, Guillain-Barre syndrome, interstitial cystitis, Kawasaki disease, lupus, Lyme disease, Meniere's disease, multiple sclerosis, myasthenia gravis, neutropenia, peripheral neuropathy, pernicious anemia, postmyocardial infaction syndrome, primary biliary cirrhosis, psoriasis, psoriatic arthritis, Raynaud's phenomenon, restless legs syndrome, rheumatic fever, rheumatoid arthritis, sarcoidosis, scleroderma, Type I diabetes, ulcerative colitis, uveitis, vasculitis, and vitiligo. Preferably the autoimmune disease is selected from the group consisting of multiple sclerosis (particularly relapsing-remitting multiple sclerosis) or psoriasis.

DETAILED DESCRIPTION OF THE DISCLOSURE

The present disclosure encompasses crystalline polymorphs of Ponesimod, processes for preparation thereof, and pharmaceutical compositions comprising at least one of, or a combination of, these solid state forms. The disclosure also relates to the conversion of Ponesimod and its solid state forms to other solid state forms of Ponesimod.

The Ponesimod and solid state forms thereof according to the present disclosure may have advantageous properties selected from at least one of the following: chemical or polymorphic purity, flowability, solubility, dissolution rate, bioviability, morphology or crystal habit, stability—such as chemical stability as well as thermal and mechanical stability with respect to polymorphic conversion, stability towards dehydration and/or storage stability, low content of residual solvent, a lower degree of hygroscopicity, flowability, and advantageous processing and handling characteristics such as compressibility, and bulk density.

A solid state form, such as a crystal form or an amorphous form, may be referred to herein as being characterized by graphical data "as depicted in" or "as substantially depicted in" a Figure. Such data include, for example, powder X-ray diffractograms and solid state NMR spectra. As is well-known in the art, the graphical data potentially provides additional technical information to further define the respective solid state form (a so-called "fingerprint") which cannot necessarily be described by reference to numerical values or peak positions alone. In any event, the skilled person will understand that such graphical representations of data may be subject to small variations, e.g., in peak relative intensities and peak positions due to certain factors such as, but not limited to, variations in instrument response and variations in sample concentration and purity, which are well known to the skilled person. Nonetheless, the skilled person would readily be capable of comparing the graphical data in the Figures herein with graphical data generated for an unknown crystal form and confirm whether the two sets of graphical data are characterizing the same crystal form or two different crystal forms. A crystal form of Ponesimod referred to herein as being characterized by graphical data "as depicted in" or "as substantially depicted in" a Figure will thus be understood to include any crystal forms of Ponesimod characterized with the graphical data having such small variations, as are well known to the skilled person, in comparison with the Figure.

A solid state form (or polymorph) may be referred to herein as polymorphically pure or as substantially free of any other solid state (or polymorphic) forms. As used herein in this context, the expression "substantially free of any other forms" will be understood to mean that the solid state Form T1 contains about 20% (w/w) or less, about 10% (w/w) or less, about 5% (w/w) or less, about 2% (w/w) or less, about 1% (w/w) or less, or about 0.5% or less or about 0% of any other forms of the subject compound as measured, for example, by XRPD. Thus, solid state Form T1 of Ponesimod described herein as substantially free of any other solid state forms would be understood to contain greater than about 80% (w/w), greater than about 90% (w/w), greater than about 95% (w/w), greater than about 98% (w/w), greater than about 99% (w/w), greater than about 99.5%, or about 100% of the subject crystalline polymorph of Ponesimod. In some embodiments of the disclosure, the described crystalline polymorph of Ponesimod may contain from about 0.5% to about 20% (w/w), from about 5% to about 20% (w/w), or from about 5% to about 10% (w/w) of one or more other solid state forms of Ponesimod.

As used hereon unless stated otherwise, reference to % values are to wt %. This is based on the assumption that the solvent % in the various forms is measured in wt %.

As used herein, and unless stated otherwise, the term "anhydrous" in relation to crystalline forms of Ponesimod, relates to a crystalline form of Ponesimod which does not include any crystalline water (or other solvents) in a defined, stoichiometric amount within the crystal. Moreover, an "anhydrous" form would typically not contain more than 1% (w/w), of either water or organic solvents as measured for example by TGA (Thermal Gravimetric Analysis).

The term "solvate," as used herein and unless indicated otherwise, refers to a crystal form that incorporates a solvent in the crystal structure. When the solvent is water, the solvate is often referred to as a "hydrate." The solvent in a solvate may be present in either a stoichiometric or in a non-stoichiometric amount.

As used herein, and unless indicated otherwise, the term "wet crystalline form" refers to a polymorph that was not dried using any conventional techniques to remove residual solvent. Examples for such conventional techniques can be, but not limited to, evaporation, vacuum drying, oven drying, drying under nitrogen flow etc.

As used herein, and unless indicated otherwise, the term "dry crystalline form" refers to a polymorph that was dried using any conventional techniques to remove residual solvent. Examples for such conventional techniques can be, but not limited to, evaporation, vacuum drying, oven drying, drying under nitrogen flow etc.

As used herein, the term "isolated" in reference to crystalline polymorph of Ponesimod of the present disclosure corresponds to a crystalline polymorph of Ponesimod that is physically separated from the reaction mixture in which it is formed.

As used herein, unless stated otherwise, the XRPD measurements are taken using copper Kα radiation wavelength 1.5418 Å. XRPD peaks reported herein are measured using CuK α radiation, λ=1.5418 Å, at a temperature of 25±3° C.

As used herein, unless stated otherwise, $^{13}$C solid state NMR was measured on 400 MHz at room temperature at a spin rate of 11 kHz.

A thing, e.g., a reaction mixture, may be characterized herein as being at, or allowed to come to "room temperature" or "ambient temperature", often abbreviated as "RT." This means that the temperature of the thing is close to, or the same as, that of the space, e.g., the room or fume hood, in which the thing is located. Typically, room temperature is from about 20° C. to about 30° C., or about 22° C. to about 27° C., or about 25° C.

The amount of solvent employed in a chemical process, e.g., a reaction or crystallization, may be referred to herein as a number of "volumes" or "vol" or "V." For example, a material may be referred to as being suspended in 10 volumes (or 10 vol or 10V) of a solvent. In this context, this expression would be understood to mean milliliters of the solvent per gram of the material being suspended, such that suspending a 5 grams of a material in 10 volumes of a solvent means that the solvent is used in an amount of 10 milliliters of the solvent per gram of the material that is being suspended or, in this example, 50 mL of the solvent. In another context, the term "v/v" may be used to indicate the number of volumes of a solvent that are added to a liquid mixture based on the volume of that mixture. For example, adding solvent X (1.5 v/v) to a 100 ml reaction mixture would indicate that 150 mL of solvent X was added.

A process or step may be referred to herein as being carried out "overnight." This refers to a time interval, e.g., for the process or step, that spans the time during the night, when that process or step may not be actively observed. This time interval is from about 8 to about 20 hours, or about 10-18 hours, typically about 16 hours.

As used herein, the term "reduced pressure" refers to a pressure that is less than atmospheric pressure. For example, reduced pressure is about 10 mbar to about 50 mbar.

Figure 7:
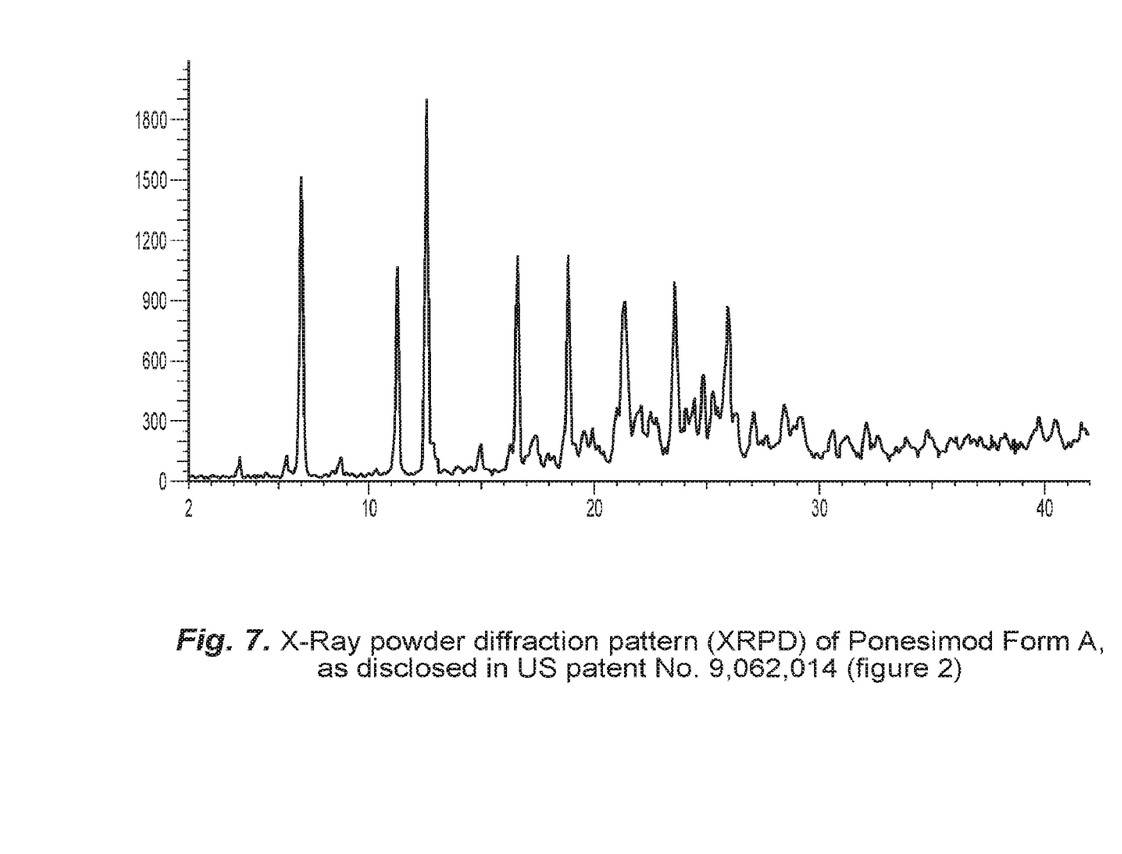
FIG. 7 shows a characteristic X-ray powder diffraction pattern (XRPD) of Ponesimod Form A, as disclosed in U.S. Pat. No. 9,062,014 (FIG. 2).

As used therein the term "Form A" of Ponesimod related to crystalline form having an XRPD shown herein in FIG. 7, as disclosed in U.S. Pat. No. 9,062,014 (FIG. 2) and in PCT application WO 2010/046835.

Figure 3:
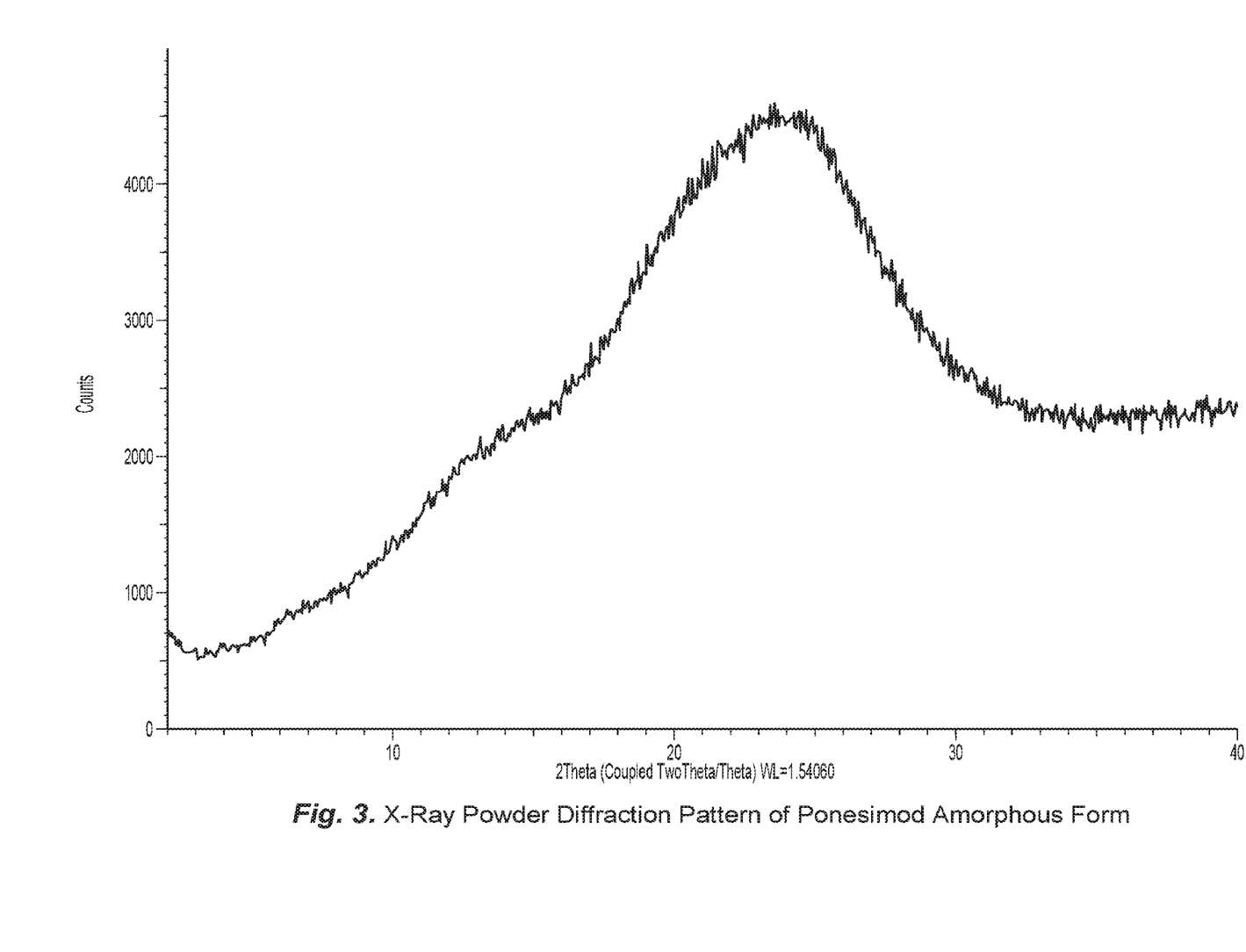
FIG. 3 shows a characteristic X-ray powder diffraction pattern (XRPD) of Ponesimod Amorphous.

As used therein the term "Amorphous Ponesimod" related to amorphous form having an XRPD shown herein in FIG.

3. Amorphous Ponesimod is described in U.S. Pat. No. 9,062,014 (FIG. 1) and in PCT application WO 2010/046835.

As used therein the term "Form C" of Ponesimod related to crystalline form disclosed in U.S. Pat. No. 9,062,014 (FIG. 3) and in PCT application WO 2010/046835.

Figure 4:
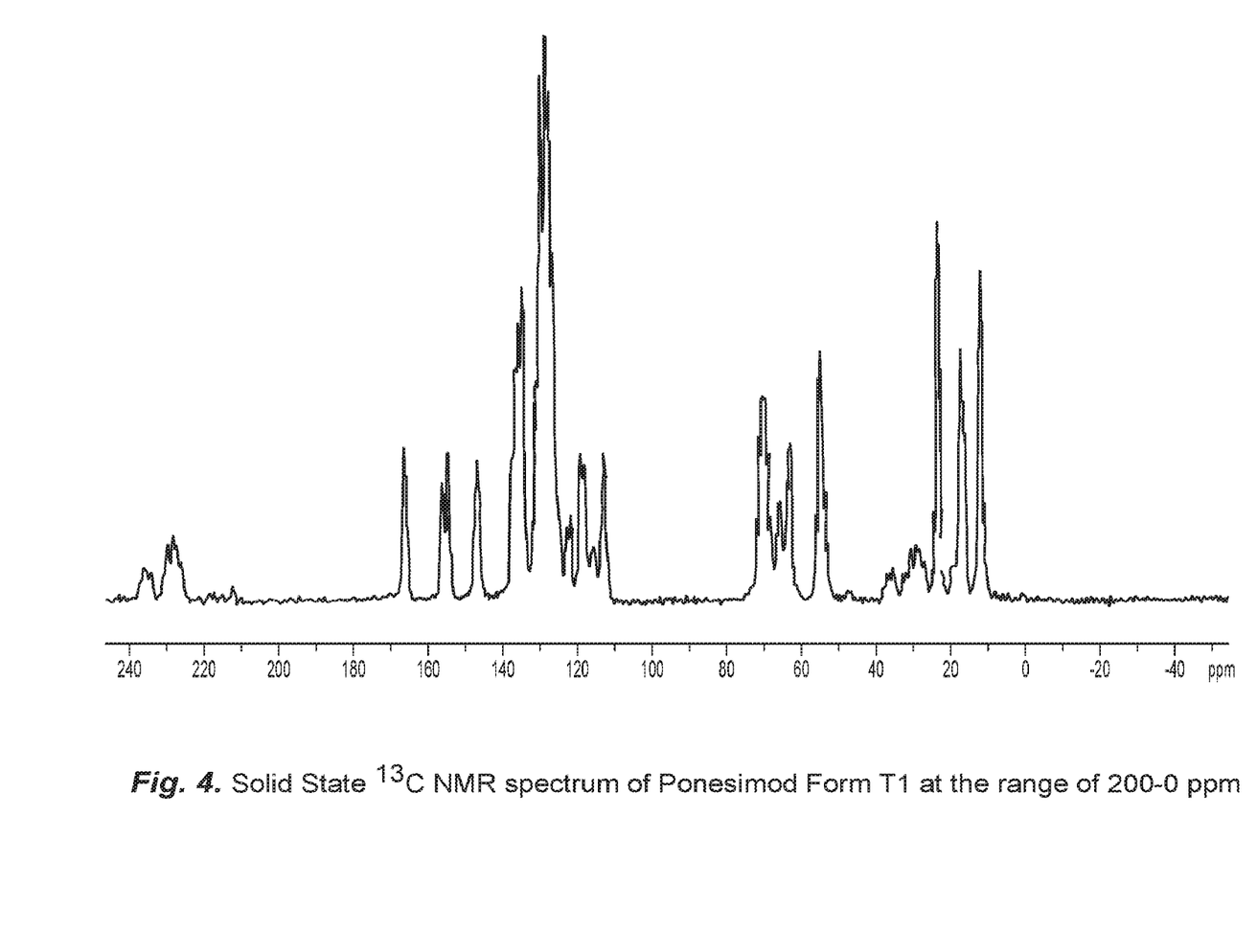
FIG. 4 shows solid state $^{13}$C-NMR spectrum of Ponesimod Form T1 at the range of 200-0 ppm.
Figure 5:
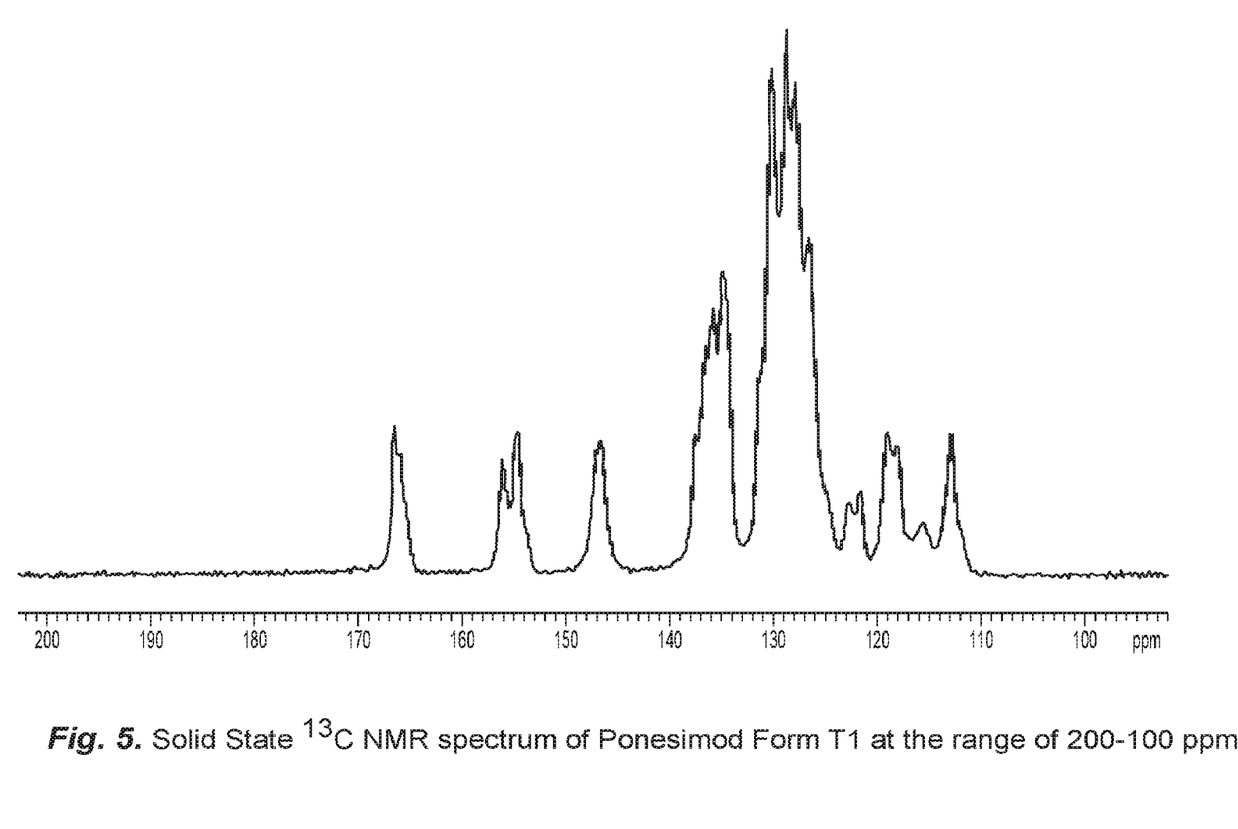
FIG. 5 shows solid state $^{13}$C-NMR spectrum of Ponesimod Form T1 at the range of 200-100 ppm.
Figure 6:
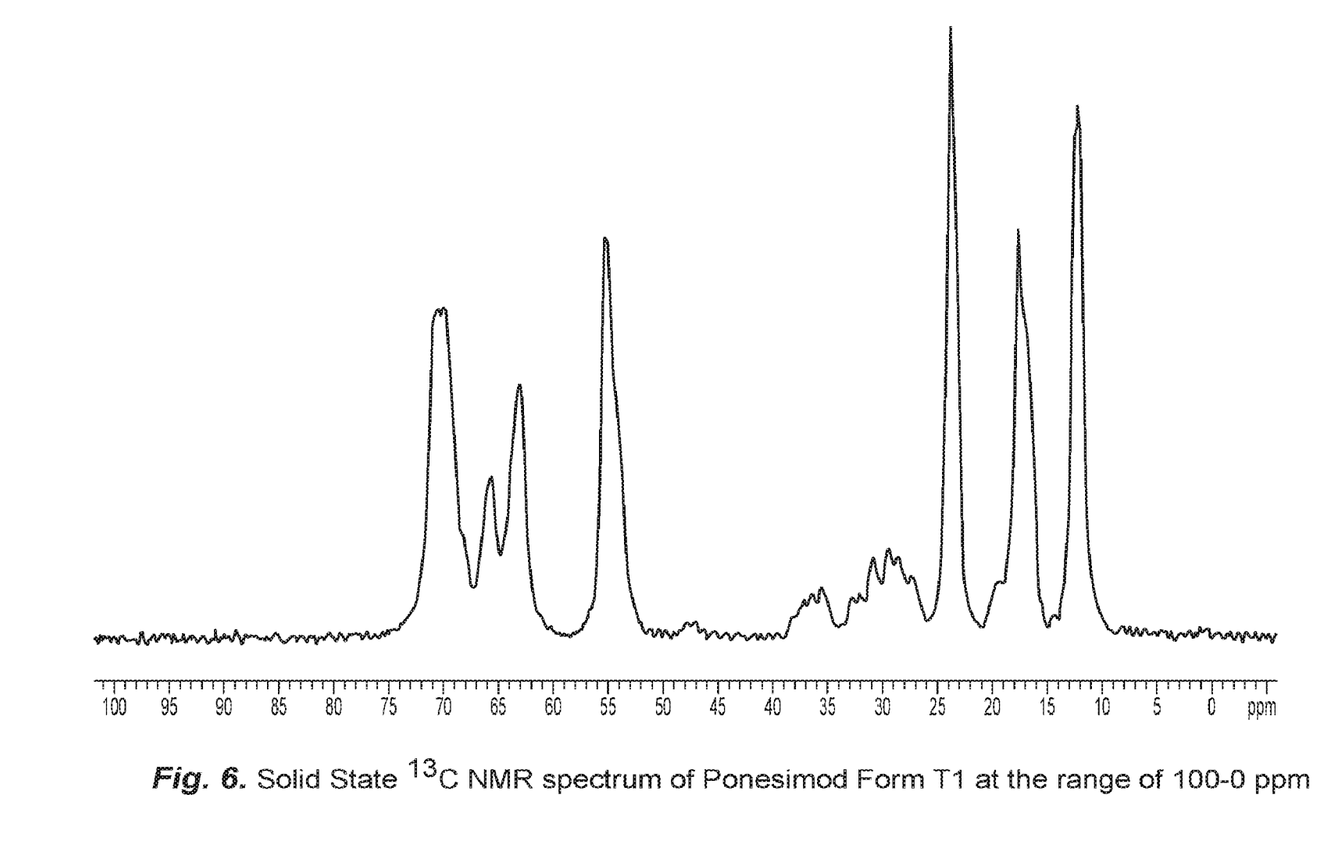
FIG. 6 shows solid state $^{13}$C-NMR spectrum of Ponesimod Form T1 at the range of 100-0 ppm.

The present disclosure comprises a crystalline polymorph of Ponesimod, designated Form T1. The crystalline Form T1 of Ponesimod may be characterized by data selected from one or more of the following: an X-ray powder diffraction pattern substantially as depicted in FIG. 1; an X-ray powder diffraction pattern having peaks at 9.1, 11.7, 17.1, 18.3 and 23.9 degrees 2-theta±0.2 degrees 2-theta; a solid-state $^{13}$C NMR spectrum with signals at 112.85, 130.17, 146.77, 154.63, 156.10 and 166.48 ppm±0.2 ppm; a solid state $^{13}$C NMR spectrum having the following chemical shift absolute differences from a peak at 23.76 ppm±2 ppm of 89.09, 106.41, 123.01, 130.87, 132.34 and 142.72 ppm±0.1 ppm; a solid-state $^{13}$C NMR spectrum as depicted in FIG. 4 or 5 or 6; and combinations of these data.

Crystalline Form T1 of Ponesimod may be further characterized by an X-ray powder diffraction pattern having peaks at 9.1, 11.7, 17.1, 18.3 and 23.9 degrees 2-theta±0.2 degrees 2-theta, and also having any one, two, three, four or five additional peaks selected from the group consisting of 2.8, 4.2, 6.2, 10.5 and 13.6 degrees 2-theta±0.2 degrees 2-theta.

Crystalline Form T1 of Ponesimod may alternatively be characterized by an XRPD pattern having peaks at 2.8, 4.2, 6.2, 9.1, 10.5, 11.7, 13.6, 17.1, 18.3 and 23.9 degrees 2-theta±0.2 degrees 2-theta.

Figure 1:
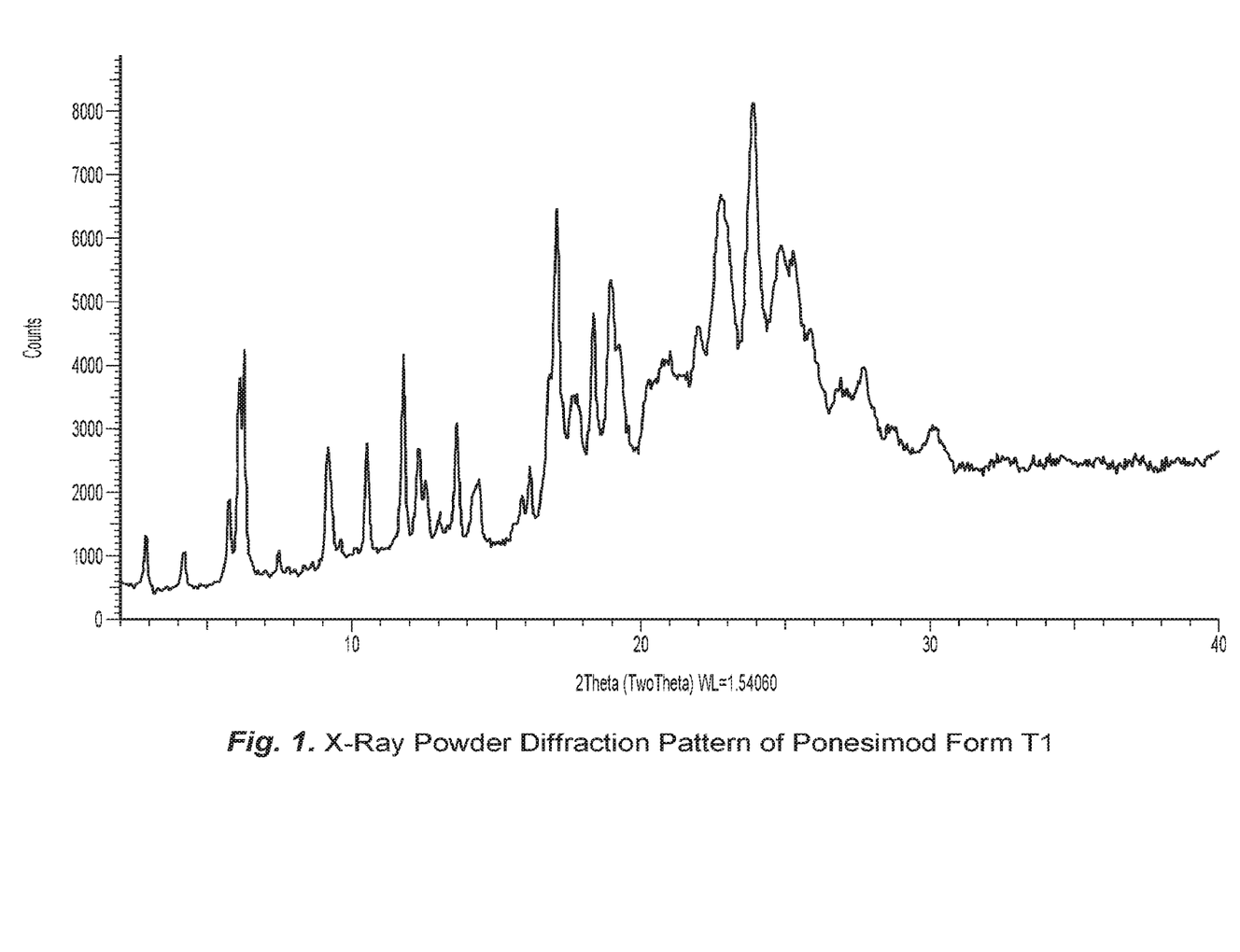
FIG. 1 shows a characteristic X-ray powder diffraction pattern (XRPD) of Ponesimod Form T1.

Crystalline Form T1 of Ponesimod may be characterized by each of the above characteristics alone/or by all possible combinations, e.g., an XRPD pattern having peaks at 9.1, 11.7, 17.1, 18.3 and 23.9 degrees 2-theta±0.2 degrees 2-theta; an XRPD pattern as depicted in FIG. 1, and combinations thereof.

In another embodiment Crystalline Ponesimod Form T1 may be characterized as anhydrous form.

In another embodiment of the present disclosure, Ponesimod Form T1 is polymorphically pure.

In one embodiment of the present disclosure, crystalline Form T1 of Ponesimod is isolated.

As discussed above, depending on which other solid state it is compared with, Form T1 of Ponesimod according to the present disclosure may have advantageous properties as described above. Ponesimod Form T1 shows unexpected higher solubility compared to other known crystalline polymorphs of Ponesimod.

The above Form T1 can be prepared by a process comprising suspending Amorphous Ponesimod in water.

Typically, 15-40 vol of water, preferably 20-38 vol or more preferably 22-35 vol of water is used for preparing Ponesimod suspension.

The suspension is preferably at a temperature of about 10 to about 40° C., preferably about 15 to about 35° C., or about 25 to about 30° C.

Typically, the suspension is kept at room temperature, preferably at 25-30° for about 1 to 40 hours, preferably for about 12 to 30 hours, more preferably for about 24 hours, optionally with stirring.

Typically, isolation of the said crystalline form may be done for example by filtering the suspension and optionally drying. Preferably, drying is done by air. Preferably, drying is performed at a temperature of about 20-45° C., preferably about 25-35° C., and more preferably about 25-30° C.

The present disclosure further comprises a crystalline polymorph of Ponesimod, designated Form T2. The crystalline Form T2 of Ponesimod may be characterized by data selected from one or more of the following: an X-ray powder diffraction pattern substantially as depicted in FIG. 2; an X-ray powder diffraction pattern having peaks at 6.8, 10.9, 11.4, 18.2 and 23.3 degrees 2-theta±0.2 degrees 2-theta; and combinations of these data Crystalline Form T2 of Ponesimod may be further characterized by an X-ray powder diffraction pattern having peaks at 6.8, 10.9, 11.4, 18.2 and 23.3 degrees 2-theta±0.2 degrees 2-theta, and also having any one, two, three, four or five additional peaks selected from the group consisting of 3.9, 4.4, 14.6, 16.4 and 21.1 degrees 2-theta±0.2 degrees 2-theta.

Crystalline Form T2 of Ponesimod may alternatively be characterized by an XRPD pattern having peaks at 3.9, 4.4, 6.8, 10.9, 11.4, 14.6, 16.4, 18.2, 21.1 and 23.3 degrees 2-theta±0.2 degrees 2-theta.

Figure 2:
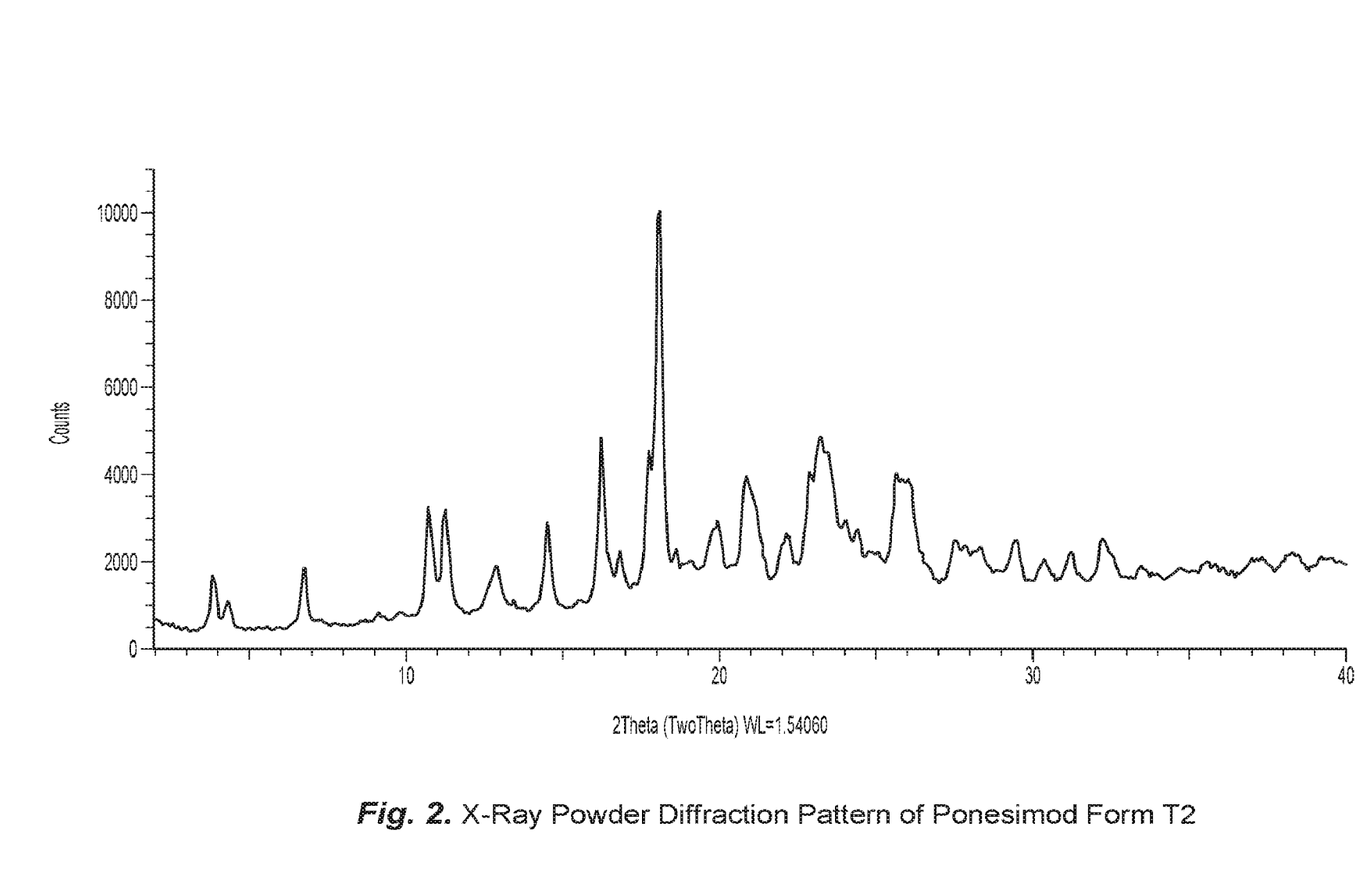
FIG. 2 shows a characteristic X-ray powder diffraction pattern (XRPD) of Ponesimod Form T2.

Crystalline Form T2 of Ponesimod may be characterized by each of the above characteristics alone/or by all possible combinations, e.g., an XRPD pattern having peaks at 6.8, 10.9, 11.4, 18.2 and 23.3 degrees 2-theta±0.2 degrees 2-theta; an XRPD pattern as depicted in FIG. 2, and combinations thereof.

In another embodiment of the present disclosure, crystalline Ponesimod Form T2 may be characterized as Tert-Butanol solvate, preferably mono-Tert Butanol solvate.

Crystalline Ponesimod may contain from about 4% to about 8% of Tert-Butanol, preferably about 7.4% of Tert-Butanol, for example as measured by TGA.

In another embodiment of the present disclosure, Ponesimod Form T1 is polymorphically pure.

In one embodiment of the present disclosure, crystalline Form T2 of Ponesimod is isolated.

The above Form T2 can be prepared by a process comprising suspending Amorphous Ponesimod in Tert-Butanol.

Typically, 4 to 10 vol of tert-butanol, preferably about 5 to 8 vol of tert-butanol, more preferably 6 vol of tert-butanol is used for preparing Ponesimod suspension.

Preferably, the temperature of the Ponesimod suspension is about 10-40° C., or about 15° C. to about 35° C. More preferably the suspension is at room temperature, and most preferably at 25-30° C.

Typically, the suspension is kept for about 24 to 100 hours, preferably for about 48 to 80 hours, or about 60 to about 75 hours, more preferably for about 70 hours, optionally with stirring.

Typically, isolation of the said crystalline form may be done for example by filtering the suspension and optionally drying. Preferably, drying is done by air. Preferably, drying is performed at a temperature of about 20-45° C., preferably about 25-35° C., and more preferably about 25-30° C.

The present invention encompasses Ponesimod crystalline forms obtainable by any of the above-described processes.

The above processes can further comprise a step of combining the Ponesimod crystalline form with at least one pharmaceutically acceptable excipient to prepare a pharmaceutical composition or a pharmaceutical formulation.

The present disclosure also relates to the uses of any one or a combination of the crystalline polymorphs of Ponesimod of the present disclosure, for preparing other crystalline polymorphs of Ponesimod. For instance, Amorphous Ponesimod can be used for the preparation of Ponesimod Forms T1 and T2.

The present disclosure also relates to any one or a combination of the above described crystalline polymorphs of Ponesimod of the present disclosure, for use in the preparation of other crystalline polymorphs of Ponesimod.

In another aspect, the present disclosure encompasses any one or combination of the above described crystalline polymorphs of Ponesimod for use in the preparation of pharmaceutical compositions and/or formulations for use in medicine, preferably for the treatment of autoimmune diseases.

In another embodiment, the present disclosure also encompasses the uses of any one or combination of the above described crystalline polymorphs of Ponesimod for the preparation of pharmaceutical compositions and/or formulations, preferably for use in medicine, preferably for the treatment of autoimmune diseases.

The present disclosure comprises processes for preparing the above mentioned pharmaceutical compositions. The processes comprise combining any one of the above crystalline polymorphs of Ponesimod and/or combinations thereof of the present disclosure with at least one pharmaceutically acceptable excipient.

Pharmaceutical formulations of the present invention contain any one or a combination of the crystalline polymorphs of Ponesimod of the present invention, particularly crystalline Ponesimod Form T1. In addition to the active ingredient, the pharmaceutical formulations of the present invention can contain one or more excipients. Excipients are added to the formulation for a variety of purposes.

Diluents increase the bulk of a solid pharmaceutical composition, and can make a pharmaceutical dosage form containing the composition easier for the patient and caregiver to handle. Diluents for solid compositions include, for example, microcrystalline cellulose (e.g. Avicel®), microfine cellulose, lactose, starch, pregelatinized starch, calcium carbonate, calcium sulfate, sugar, dextrates, dextrin, dextrose, dibasic calcium phosphate dihydrate, tribasic calcium phosphate, kaolin, magnesium carbonate, magnesium oxide, maltodextrin, mannitol, polymethacrylates (e.g. Eudragit®), potassium chloride, powdered cellulose, sodium chloride, sorbitol, and talc.

Solid pharmaceutical compositions that are compacted into a dosage form, such as a tablet, can include excipients whose functions include helping to bind the active ingredient and other excipients together after compression. Binders for solid pharmaceutical compositions include acacia, alginic acid, carbomer (e.g. carbopol), carboxymethylcellulose sodium, dextrin, ethyl cellulose, gelatin, guar gum, hydrogenated vegetable oil, hydroxyethyl cellulose, hydroxypropyl cellulose (e.g. Klucel®), hydroxypropyl methyl cellulose (e.g. Methocel®), liquid glucose, magnesium aluminum silicate, maltodextrin, methylcellulose, polymethacrylates, povidone (e.g. Kollidon®, Plasdone®), pregelatinized starch, sodium alginate, and starch.

The dissolution rate of a compacted solid pharmaceutical composition in the patient's stomach can be increased by the addition of a disintegrant to the composition. Disintegrants include alginic acid, carboxymethylcellulose calcium, carboxymethylcellulose sodium (e.g. Ac-Di-Sol®, Primellose®), colloidal silicon dioxide, croscarmellose sodium, crospovidone (e.g. Kollidon®, Polyplasdone®), guar gum, magnesium aluminum silicate, methyl cellulose, microcrystalline cellulose, polacrilin potassium, powdered cellulose, pregelatinized starch, sodium alginate, sodium starch glycolate (e.g. Explotab®), and starch.

Glidants can be added to improve the flowability of a non-compacted solid composition and to improve the accuracy of dosing. Excipients that can function as glidants include colloidal silicon dioxide, magnesium trisilicate, powdered cellulose, starch, talc, and tribasic calcium phosphate.

When a dosage form such as a tablet is made by the compaction of a powdered composition, the composition is subjected to pressure from a punch and dye. Some excipients and active ingredients have a tendency to adhere to the surfaces of the punch and dye, which can cause the product to have pitting and other surface irregularities. A lubricant can be added to the composition to reduce adhesion and ease the release of the product from the dye. Lubricants include magnesium stearate, calcium stearate, glyceryl monostearate, glyceryl palmitostearate, hydrogenated castor oil, hydrogenated vegetable oil, mineral oil, polyethylene glycol, sodium benzoate, sodium lauryl sulfate, sodium stearyl fumarate, stearic acid, talc, and zinc stearate.

Flavoring agents and flavor enhancers make the dosage form more palatable to the patient. Common flavoring agents and flavor enhancers for pharmaceutical products that can be included in the composition of the present invention include maltol, vanillin, ethyl vanillin, menthol, citric acid, fumaric acid, ethyl maltol, and tartaric acid.

Solid and liquid compositions can also be dyed using any pharmaceutically acceptable colorant to improve their appearance and/or facilitate patient identification of the product and unit dosage level.

In liquid pharmaceutical compositions of the present invention, Ponesimod and any other solid excipients are dissolved or suspended in a liquid carrier such as water, vegetable oil, alcohol, polyethylene glycol, propylene glycol, or glycerin.

Liquid pharmaceutical compositions can contain emulsifying agents to disperse uniformly throughout the composition an active ingredient or other excipient that is not soluble in the liquid carrier. Emulsifying agents that can be useful in liquid compositions of the present invention include, for example, gelatin, egg yolk, casein, cholesterol, acacia, tragacanth, chondrus, pectin, methyl cellulose, carbomer, cetostearyl alcohol, and cetyl alcohol.

Liquid pharmaceutical compositions of the present invention can also contain a viscosity enhancing agent to improve the mouth-feel of the product and/or coat the lining of the gastrointestinal tract. Such agents include acacia, alginic acid bentonite, carbomer, carboxymethylcellulose calcium or sodium, cetostearyl alcohol, methyl cellulose, ethylcellulose, gelatin guar gum, hydroxyethyl cellulose, hydroxypropyl cellulose, hydroxypropyl methyl cellulose, maltodextrin, polyvinyl alcohol, povidone, propylene carbonate, propylene glycol alginate, sodium alginate, sodium starch glycolate, starch tragacanth, and xanthan gum.

Sweetening agents such as sorbitol, saccharin, sodium saccharin, sucrose, aspartame, fructose, mannitol, and invert sugar can be added to improve the taste.

Preservatives and chelating agents such as alcohol, sodium benzoate, butylated hydroxyl toluene, butylated hydroxyanisole, and ethylenediamine tetraacetic acid can be added at levels safe for ingestion to improve storage stability.

According to the present invention, a liquid composition can also contain a buffer such as gluconic acid, lactic acid, citric acid, or acetic acid, sodium gluconate, sodium lactate, sodium citrate, or sodium acetate. Selection of excipients and the amounts used can be readily determined by the formulation scientist based upon experience and consideration of standard procedures and reference works in the field.

The solid compositions of the present invention include powders, granulates, aggregates, and compacted compositions. The dosages include dosages suitable for oral, buccal, rectal, parenteral (including subcutaneous, intramuscular, and intravenous), inhalant, and ophthalmic administration. Although the most suitable administration in any given case will depend on the nature and severity of the condition being treated, the most preferred route of the present invention is oral. The dosages can be conveniently presented in unit dosage form and prepared by any of the methods well-known in the pharmaceutical arts.

Dosage forms include solid dosage forms like tablets, powders, capsules, suppositories, sachets, troches, and lozenges, as well as liquid syrups, suspensions, and elixirs.

The dosage form of the present invention can be a capsule containing the composition, preferably a powdered or granulated solid composition of the invention, within either a hard or soft shell. The shell can be made from gelatin and optionally contain a plasticizer such as glycerin and sorbitol, and an opacifying agent or colorant.

The active ingredient and excipients can be formulated into compositions and dosage forms according to methods known in the art.

A composition for tableting or capsule filling can be prepared by wet granulation. In wet granulation, some or all of the active ingredients and excipients in powder form are blended and then further mixed in the presence of a liquid, typically water, which causes the powders to clump into granules. The granulate is screened and/or milled, dried, and then screened and/or milled to the desired particle size. The granulate can then be tableted, or other excipients can be added prior to tableting, such as a glidant and/or a lubricant.

A tableting composition can be prepared conventionally by dry blending. For example, the blended composition of the actives and excipients can be compacted into a slug or a sheet and then comminuted into compacted granules. The compacted granules can subsequently be compressed into a tablet.

As an alternative to dry granulation, a blended composition can be compressed directly into a compacted dosage form using direct compression techniques. Direct compression produces a more uniform tablet without granules. Excipients that are particularly well suited for direct compression tableting include microcrystalline cellulose, spray dried lactose, dicalcium phosphate dihydrate, and colloidal silica. The proper use of these and other excipients in direct compression tableting is known to those in the art with experience and skill in particular formulation challenges of direct compression tableting.

A capsule filling of the present invention can comprise any of the aforementioned blends and granulates that were described with reference to tableting, but they are not subjected to a final tableting step.

A pharmaceutical formulation of Ponesimod can be administered. Ponesimod is preferably formulated for administration to a mammal, preferably a human, by injection. Ponesimod can be formulated, for example, as a viscous liquid solution or suspension, preferably a clear solution, for injection. The formulation can contain one or more solvents. A suitable solvent can be selected by considering the solvent's physical and chemical stability at various pH levels, viscosity (which would allow for syringeability), fluidity, boiling point, miscibility, and purity. Suitable solvents include alcohol USP, benzyl alcohol NF, benzyl benzoate USP, and Castor oil USP. Additional substances can be added to the formulation such as buffers, solubilizers, and antioxidants, among others. Ansel et al., Pharmaceutical Dosage Forms and Drug Delivery Systems, 7th ed.

The crystalline polymorphs of Ponesimod and the pharmaceutical compositions of Ponesimod of the present disclosure can be used as medicaments, particularly in the treatment of autoimmune diseases.

In another embodiment, Ponesimod Form T1 and the pharmaceutical compositions of Ponesimod Form T1 can be used as medicaments, particularly in the treatment of autoimmune diseases.

The present disclosure also provides methods of treating autoimmune diseases comprising administering a therapeutically effective amount of crystalline polymorphs of Ponesimod of the present disclosure, or at least one of the above pharmaceutical compositions, to a subject in need of the treatment.

Having thus described the disclosure with reference to particular preferred embodiments and illustrative examples, those in the art can appreciate modifications to the disclosure as described and illustrated that do not depart from the spirit and scope of the disclosure as disclosed in the specification. The Examples are set forth to aid in understanding the disclosure but are not intended to, and should not be construed to limit its scope in any way.

Analytical Methods

Powder X-Ray Diffraction (XRD) Method

X-ray diffraction was performed on X-Ray powder diffractometer: Bruker D8 Advance; CuK radiation ($\lambda$=1.5418 Å); Lynx eye detector; laboratory temperature 22-25° C.; PMMA specimen holder ring. Prior to analysis, the samples were gently ground by means of mortar and pestle in order to obtain a fine powder. The ground sample was adjusted into a cavity of the sample holder and the surface of the sample was smoothed by means of a cover glass. Measurement parameters:

Scan range: 2-40 degrees 2-theta;
Scan mode: continuous;
Step size: 0.05 degrees;
Time per step: 0.5 s;
Sample spin: 30 rpm;
Sample holder: PMMA specimen holder ring.

Thermal Gravimetric Analysis (TGA) Method

Thermogravimetric analysis was conducted on a TA instrument Q500 thermogravimetric analyzer. About 5-10 mg sample was placed into a tarred TGA crucible and placed into a TGA furnace. The furnace was heated under nitrogen at a heating rate of 10° C./min up to 250° C.

Solid-State $^{13}$C NMR

Solid-state $^{13}$C NMR spectra were recorded with variable amplitude cross polarization, magic angle spinning and high power proton decoupling using a BRUKER Avance III+ spectrometer operating at 400 MHZ at room temperature. A probe using 4 mm O.D. ZrO$_2$ zirconia rotors was employed. The operation conditions were: contact time: 3 ms; recycle delay: 2 s; 5100 scans and spin rate of 11 KHz. Chemical shifts were referenced via a replacement sample of glycine (carboxyl carbon chemical shift assigned as 176.03 ppm relative to the signal of tetramethylsilane).

Solubility Measurement

The solubility for Ponesimod Form T1, according to this invention, Ponesimod Form A and Form C (described in PCT application WO 2010/046835) was measured by using Dissolution apparatus (Lab India DS8000) at 37° C. Buffers at pH. 1.2, 4.5 and 6.8 were prepared as per the USP 36 Solutions/Buffer Solutions 1209. About 200 mg of Ponesimod Form T1, 150 mg of Ponesimod Forms A and C were added to the 100 mL buffer (pH 1.2, 4.5 and 6.8) in individual flasks to obtain saturated suspension and the suspension was stirred with 250 rpm for 24 hours. Suspension was observed though out stirring period. Samples were drawn at different intervals on completion of 15 mins, 30 mins, 45 mins, 1 hrs, 2 hrs, 3 hrs, 4 hrs and 24 hrs from each flask and filtered through 0.45µ PTFE filter, each solution was analyzed for Ponesimod content by liquid chromatography. Only the solubility measured at pH=1.2 is shown here since Ponesimod is not soluble at higher pH conditions (e.g. 4.5 and 6.8).

TABLE I

Solubility results For Ponesimod measured at pH = 1.2

| Polymorph | Solubility results at pH = 1.2 (mg/ml) | | | | | | | |
|---|---|---|---|---|---|---|---|---|
| | 15 Min | 30 Min | 45 Min | 60 Min | 2 Hrs | 3 Hrs | 4 Hrs | 24 Hrs |
| T1 (anhydrous) | 0.07 | 0.09 | 0.12 | 0.15 | 0.24 | 0.29 | 0.31 | 0.40 |
| C (anhydrous) | 0.05 | 0.06 | 0.07 | 0.08 | 0.09 | 0.11 | 0.12 | 0.15 |
| A (hydrate) | 0.12 | 0.13 | 0.12 | 0.12 | 0.11 | 0.11 | 0.11 | 0.12 |

TABLE II

Method of analysis of Liquid chromatography

| Column: | Aquity CSH Phenyl hexyl (100*2.1) mm 1.7 u |
|---|---|
| Flow | 0.25 ml/min |
| Eluent A | 0.10% Perchloric acid in water |
| Eluent B | Acetonitrile:Methanol (7:3) |
| Injection Volume | 1.0 µl |
| Detector | 220 nm |
| Column temperature | 35° C. |
| Auto sampler temperature | 20° C. |
| Detector run time | 12.0 minutes |
| Diluent | Methanol |

| Time | A % | B % |
|---|---|---|
| 0 | 70 | 30 |
| 25 | 20 | 80 |
| 34.9 | 10 | 90 |
| 35 | 70 | 30 |

EXAMPLES

Amorphous Ponesimod was used as the starting material for the preparation of Ponesimod Forms T1 and T2. Amorphous Ponesimod can be prepared according to the procedure described in U.S. Pat. No. 9,062,014 (Example 1) and in PCT application WO 2010/046835. Amorphous Ponesimod can optionally be prepared by the procedure described herein.

Preparation of Amorphous form

Ponesimod (Form A, commercially available) 2.0 gr and 20 ml of Dichloromethane were added in flask, stirred for 10 min at 40° C. to obtain a clear solution. The obtained clear solution was filtered under vacuum and distilled off the solvent under vacuum (less than 10 mbar) at 40° C. in 15 min. The obtained solid was dried at 40° C. for 5 hrs under vacuum to obtain Ponesimod as Amorphous form (1.8 gr, FIG. 3).

Example 1. Preparation of Ponesimod Form T1

Ponesimod (Amorphous form) 0.15 gr was added to 5 ml of Water at 25-30° C. and the obtained slurry was stirred for 24 hrs at 25-30° C. The obtained solid was filtered under vacuum and kept under suction for about 20 minutes at 25-30° C. to obtain Ponesimod (0.10 gr). The obtained solid was analyzed by XRPD and confirmed Form T1 (FIG. 1).

Example 2. Preparation of Ponesimod Form T2

Ponesimod (Amorphous form) 0.5 gr was added in 3 ml of tert-Butanol at 25-30° C. and the obtained slurry was stirred for 70 hrs at 25-30° C. The obtained solid was filtered under vacuum and kept under suction for about 20 minutes at 25-30° C. to obtain Ponesimod (0.4 gr). The obtained solid was analyzed by XRPD and confirmed Form T2 (FIG. 2).

Example 3. Preparation of Ponesimod Form T1

Ponesimod (Amorphous form) 2.0 gr was added to 50 ml of Water at 25-30° C. and the obtained slurry was stirred for 24 hrs at 25-30° C. The obtained solid was filtered under vacuum and kept under suction for about 20 minutes at 25-30° C. and dried at 25-30° C. in air tray dryer for 2 hr to obtain Ponesimod 1.20 gr. XRPD measurement confirmed Form T1 content.

The invention claimed is:

1. A crystalline form of Ponesimod designated as Form T1, characterized by data selected from one or more of the following:
   a) an X-ray powder diffraction pattern having peaks at 9.1, 11.7, 17.1, 18.3 and 23.9 degrees 2-theta ±0.2 degrees 2-theta;
   b) an XRPD pattern as depicted in FIG. 1;
   c) a solid state $^{13}$C-NMR spectrum having characteristic peaks at 112.85, 130.17, 146.77, 154.63, 156.10 and 166.48 ppm ±0.2 ppm;
   d) a solid state $^{13}$C-NMR spectrum having the following chemical shift absolute differences from a reference peak at 23.76 ppm ±2 ppm of 89.09, 106.41, 123.01, 130.87, 132.34 and 142.72 ppm ±0.1 ppm;
   e) a solid state $^{13}$C-NMR spectrum as depicted in FIG. 4 or 5 or 6; and
   f) a combination of any two or more of the above.

2. The crystalline Form T1 of Ponesimod according to claim 1, characterized by an XRPD pattern having peaks at 9.1, 11.7, 17.1, 18.3 and 23.9 degrees 2-theta ±0.2 degrees 2-theta, and also having any one, two, three, four or five additional peaks selected from the group consisting of 2.8, 4.2, 6.2, 10.5 and 13.6 degrees 2-theta ±0.2 degrees 2-theta.

3. A pharmaceutical composition comprising a crystalline form according to claim 1.

4. A pharmaceutical formulation comprising a crystalline form according to claim 1 and at least one pharmaceutically acceptable excipient.

5. The crystalline form according to claim 1 for use as a medicament.

6. The crystalline form according to claim 1, for use in the treatment of autoimmune diseases.

7. The crystalline form according to claim 1 for the manufacture of a medicament for treatment of autoimmune diseases.

8. A process for preparing a pharmaceutical formulation, comprising combining a crystalline form according to claim 1 with at least one pharmaceutically acceptable excipient.

9. A method of treating autoimmune diseases, comprising administering a therapeutically effective amount of a crystalline form according to claim 1 to a subject suffering from autoimmune diseases.

* * * * *